United States Patent
Jain

(10) Patent No.: US 10,463,658 B2
(45) Date of Patent: Nov. 5, 2019

(54) METHOD OF INHIBITING FLT3 KINASE

(71) Applicant: AROG Pharmaceuticals, LLC, Dallas, TX (US)

(72) Inventor: Vinay K. Jain, Dallas, TX (US)

(73) Assignee: VIDERA PHARMACEUTICALS, LLC, Dallas, TX (US)

( * ) Notice: Subject to any disclaimer, the term of this patent is extended or adjusted under 35 U.S.C. 154(b) by 178 days.

(21) Appl. No.: 14/447,139

(22) Filed: Jul. 30, 2014

(65) Prior Publication Data

US 2015/0119421 A1 Apr. 30, 2015

Related U.S. Application Data

(60) Provisional application No. 61/895,820, filed on Oct. 25, 2013.

(51) Int. Cl.
| | |
|---|---|
| A61K 31/4709 | (2006.01) |
| A61K 45/06 | (2006.01) |
| G01N 33/50 | (2006.01) |
| G01N 33/574 | (2006.01) |
| A61K 31/404 | (2006.01) |
| A61K 31/44 | (2006.01) |
| A61K 31/496 | (2006.01) |
| A61K 31/517 | (2006.01) |
| A61K 31/5377 | (2006.01) |
| A61K 31/553 | (2006.01) |

(52) U.S. Cl.
CPC ........ *A61K 31/4709* (2013.01); *A61K 31/404* (2013.01); *A61K 31/44* (2013.01); *A61K 31/496* (2013.01); *A61K 31/517* (2013.01); *A61K 31/5377* (2013.01); *A61K 31/553* (2013.01); *A61K 45/06* (2013.01); *G01N 33/5011* (2013.01); *G01N 33/574* (2013.01); *G01N 33/57426* (2013.01); *G01N 2333/912* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,990,146 A | 11/1999 | Boschellie et al. | |
| 7,071,337 B2 | 7/2006 | Kath et al. | |
| 7,183,414 B2 | 2/2007 | Tom et al. | |
| 2004/0049032 A1 | 3/2004 | Charrier | |
| 2005/0020570 A1* | 1/2005 | Griffin | A61K 31/407 514/211.08 |

FOREIGN PATENT DOCUMENTS

| | | |
|---|---|---|
| WO | 1999/016755 | 4/1999 |
| WO | 2001/040217 A1 | 6/2001 |
| WO | 2002/032861 A2 | 4/2002 |
| WO | 2002/092599 A1 | 11/2002 |
| WO | 2003/024931 A1 | 3/2003 |
| WO | 2003/024969 A1 | 3/2003 |
| WO | 2003/099771 A2 | 4/2003 |
| WO | 2003/035009 A2 | 5/2003 |
| WO | 2003/037347 A1 | 5/2003 |
| WO | 2003/057690 A1 | 7/2003 |
| WO | 2004/005281 A1 | 1/2004 |
| WO | 2004/016597 A2 | 2/2004 |
| WO | 2004/018419 A2 | 3/2004 |
| WO | 2004/039782 A1 | 5/2004 |
| WO | 2004/043389 A2 | 5/2004 |
| WO | 2004/046120 A2 | 6/2004 |
| WO | 2004/058749 A1 | 7/2004 |

OTHER PUBLICATIONS

Pauwels et al., "Identification of novel FLT3 kinase inhibitors", Eur.J.Med.Chem., 2013, vol. 63, pp. 713-721; published online Mar. 21, 2013.*
Nishioka et al., Leukemia, 2007, vol. 21, pp. 1308-1310.*
Ocio et al., Lancet Oncology, 2008, vol. 9, No. 12, pp. 1157-1165.*
Ding et al., Blood, 2010, vol. 116, No. 16, pp. 2984-2993.*
Giles et al., Leukemia, 2009, vol. 23, pp. 1698-1707.*
Levis, "FLT3 mutations in acute myeloid leukemia: what is the best approach in 2013?" ASH Education Book, Dec. 6, 2013, vol. 2013, No. 1, pp. 220-226 (Year: 2013).*
Small, "FLT3 Mutations: Biology and Treatment", ASH Education Book, Jan. 1, 2006, vol. 2006, No. 1, pp. 178-184 (Year: 2006).*
Australian Patent Office (ISA), International Search Report and Written Opinion for PCT/US2014/049213 dated Nov. 18, 2014, 12 pp.

(Continued)

*Primary Examiner* — Jeffrey S Lundgren
*Assistant Examiner* — Stephanie K Springer
(74) *Attorney, Agent, or Firm* — Edwin S. Flores; Daniel J. Chalker; Chalker Flores, LLP

(57) ABSTRACT

The present invention includes a method of inhibiting or reducing deregulated FLT3 tyrosine kinase activity or FLT3 tyrosine kinase expression in a subject with a proliferative disease by administering to the subject having or suspected to have the proliferative disease, a therapeutically or prophylactically effective amount of the compound (CP-673,451) of Formula I:

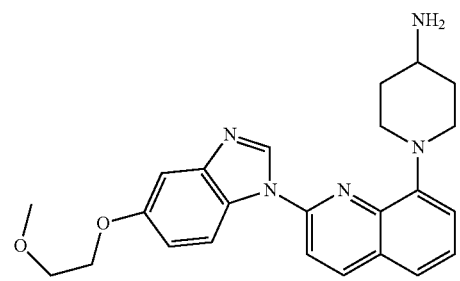

or pharmaceutically acceptable salt thereof.

17 Claims, 5 Drawing Sheets

Specification includes a Sequence Listing.

(56) References Cited

OTHER PUBLICATIONS

Roberts, et al. "Antiangiogenic and Antitumor Activity of a Selective PDGFR Tyrosine Kinase Inhibitor, CP-673,451" Cancer Res 2005; 65: (3). Feb. 1, 2005.
Schittenhelm, et al. "FLT3 K663Q is a novel AML-associated oncogenic kinase: determination of biochemical properties and sensitivity to Sunitinib (SU11248)" Leukemia (2006) vol. 20, No. 11, pp. 2008-2014.
Abu-Duhier, et al. "FLT3 internal tandem duplication mutations in adult acute myeloid leukemia define a high risk group" British Journal of Haematology. 2000; 111:190-195.
Bacher, et al. "Prognostic relevance of FLT3-TKD mutations in AML: the combination matters—an analysis of 3082 patients" Blood. 2008; 111:2527-2537.
Bains, et al. "FLT3 and NPM1 mutations in myelodysplastic syndromes: Frequency and potential value for predicting progression to acute myeloid leukemia" American Journal of Clinical Pathology. Jan. 2011; 135:62-69.
Cancer Genome Atlas Research Network. Genomic and Epigenetic Landscapes of Adult De Novo Acute Myelod Leukemia. N Eng J Med. May 30, 2013;388: 2059-74.
Carter, et al. "Inhibition of drug-resistant mutants of ABL, KIT, and EGF receptor kinases" Proc. Natl. Acad. Sci. USA. Aug. 2, 2005; 102:11011-11016.
Fabian, et al. "A small molecule-kinases interaction map for clinical kinase inhibitors" Nat Biotechnol. Mar. 2005; 23:329-336.
Gilliland, et al. "The roles of FLT3 in hematopoiesis and leukemia" Blood. 2002; 100:1532-1542.
Karaman, et al. "A quantitative analysis of kinase inhibitor selectivity" Nat Biotechnol 2008; 26:127-132.
Kindler, et al. "FLT3 as a therapeutic target in AML: still challenging after all these years" Blood. Dec. 9, 2010; 116: 5089-102.
Kiyoi, et al. "Internal tandem duplication of the FLT3 associated with luekocytosis in acute promyelocytic leukemia" Leukemia Study Group on the Ministry of Health and Welfare Kohseisho Leukemia. 1997; 11: 1447-1452.
Kiyoi, et al. "Internal tandem duplication of the FLT3 gene is a novel modality of elongation mutation which causes constitutive activation of the product" Leukemia. 1998; 12: 1333-1337.
Kiyoi, et al. "Prognostic implication of FLT3 and N-RAS gene mutations in acute myeloid leukemia" Blood. May 1, 1999; 93:3074-3080.
Kottaridis, et al. The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials. Blood. Sep. 15, 2001; 98: 1742-1759.
Liu, et al. "Rational design of inhibitors that bind to inactive kinase conformations" Nature Chem. Biol. Published online Jun. 16, 2006; 2:358-354.
Manley, et al. "Advances in the structural biology, design and clinical development of Bcr-Abl kinase inhibitors for the treatment of chronic myeloid leukaemia" Biochim. Biophis. Acta. 2005;1754:3-13.
Patel, et al. Prognostic Relevance of Integrated Genetic Profiling in Acute Myeloid Leukemia. N Eng J Med. Mar. 22, 2012; 366:1079-1089.
Schnittger, et al. "Analysis of FLT3 length mutations in 1003 patients with acute myeloid leukemia: correlation to cytogenetics, FAB subtype, and prognosis in the AMLCG study and usefulness as a marker for the detection of minimal residual disease" Blood. Jul. 1, 2002; 100:59-66.
Thiede, et al. "Analysis of FLT3-activating mutations in 979 patients with acute myelogenous leukemia: association with FAB subtypes and identification of subgroups with poor prognosis" Blood. 2002; 99:4326-4335.
Wan, et al. "Mechanism of activation of the RAF-ERK signaling pathway by oncogenic mutations of B-RAF" Cell. Mar. 19, 2004;116:855-867.
Yamamoto, et al. "Activating mutation of D835 within the activation loop of FLT3 in human hematologic malignancies" Blood. Apr. 15, 2001; 97:2434-2439.
Zhang, et al. "Targeting cancer with small molecule kinase inhibitors" Nature Reviews Cancer. Jan. 2009; 9:28-39.

* cited by examiner

METHOD OF INHIBITING FLT3 KINASE

CROSS-REFERENCE TO RELATED APPLICATIONS

This application claims priority to U.S. Provisional Application Ser. No. 61/895,820 filed Oct. 25, 2013, the entire contents of which are incorporated herein by reference.

TECHNICAL FIELD OF THE INVENTION

The present invention relates to methods of reducing or inhibiting the kinase activity of normal and mutated FLT3 in a cell or a subject, and the use of such methods for preventing or treating cell proliferative disorder (s) related to FLT3.

STATEMENT OF FEDERALLY FUNDED RESEARCH

None.

REFERENCE TO A SEQUENCE LISTING

The present application includes a Sequence Listing filed separately as required by 37 CFR 1.821-1.825.

INCORPORATION-BY-REFERENCE OF MATERIALS FILED ON COMPACT DISC

None.

BACKGROUND OF THE INVENTION

Without limiting the scope of the invention, its background is described in connection with receptor tyrosine kinases.

The FMS-like tyrosine kinase 3 (FLT3) gene encodes a membrane bound receptor tyrosine kinase that affects hematopoiesis leading to hematological disorders and malignancies. See Drexler, H G et al. Expression of FLT3 receptor and response to FLT3 ligand by leukemic cells. Leukemia. 1996; 10:588-599; Gilliland, D G and J D Griffin. The roles of FLT3 in hematopoiesis and leukemia. Blood. 2002; 100:1532-1542; Stirewalt, D L and J P Radich. The role of FLT3 in hematopoietic malignancies. Nat Rev Cancer. 2003; 3:650-665. Activation of FLT3 receptor tyrosine kinases is initiated through the binding of the FLT3 ligand (FLT3L) to the FLT3 receptor which is expressed on hematopoietic progenitor and stem cells.

FLT3 is one of the most frequently mutated genes in hematological malignancies, present in approximately 30% of adult acute myeloid leukemia (AML). See Patel, J P et al. Prognostic relevance of integrated genetic profiling in acute myeloid leukemia. N Eng J Med. 2012; 366:1079-1089; Cancer Genome Atlas Research Network. Genomic and epigenetic landscapes of adult de novo acute myelod leukemia. N Eng J Med. 2013; 388: 2059-74. FLT3 mutations have been detected in approximately 2% of patients diagnosed with intermediate and high risk myelodysplastic syndrome (MDS). See S Bains, Luthra R, Medeiros L J and Zuo Z. FLT3 and NPM1 mutations in myelodysplastic syndromes: Frequency and potential value for predicting progression to acute myeloid leukemia. American Journal of Clinical Pathology. January 2011; 135:62-69; P K Bhamidipati, Daver N G, Kantarjian H, et al. FLT3 mutations in myelodysplastic syndromes (MDS) and chronic myelomonocytic leukemia (CMML). 2012. Journal of Clinical Oncology. Suppl; abstract 6597. Similar to MDS, the number of FLT3 mutations in patients with acute promyelocytic leukemia (APL) is less than 5%. The most common FLT3 mutations are internal tandem duplications (ITDs) that lead to in-frame insertions within the juxtamembrane domain of the FLT3 receptor. FLT3-ITD mutations have been reported in 15-35% of adult AML patients. See Nakao M, S Yokota and T Iwai. Internal tandem duplication of the FLT3 gene found in acute myeloid leukemia. Leukemia. 1996; 10:1911-1918; H Kiyoi, M Towatari and S Yokota. Internal Tandem duplication of the FLT3 gene is a novel modality of elongation mutation, which causes constitutive activation of the product. Leukemia. 1998; 12:1333-1337. A FLT3-ITD mutation is an independent predictor of poor patient prognosis and is associated with increased relapse risk after standard chemotherapy, and decreased disease free and overall survival. See FM Abu-Duhier, Goodeve A C, Wilson G A, et al. FLT3 internal tandem duplication mutations in adult acute myeloid leukemia define a high risk group. British Journal of Haematology. 2000; 111:190-195; H Kiyoi, T Naoe, Y Nakano, et al. Prognostic implication of FLT3 and N-RAS gene mutations in acute myeloid leukemia. Blood. 1999; 93:3074-3080. Less frequent are FLT3 point mutations that arise in the activation loop and gatekeeper region of the FLT3 receptor. The most commonly affected activation loop codon is aspartate 835 (D835). The most frequently mutated codon in the receptor gatekeeper region is phenylalanine 691 (F691). Nucleotide substitutions of the D835 and F691I residues occur in approximately 5-10% of adult acute myeloid leukemia patients. See Y Yamamoto, H Kiyoi and Y Nakano, et al. Activating mutation of D835 within the activation loop of FLT3 in human hematologic malignancies. Blood. 2001; 97:2434-2439; C Thiede, Steudal C, Mohr B, et al. Analysis of FLT3-activating mutations in 979 patients with acute myelogenous leukemia: association with FAB subtypes and identification of subgroups with poor prognosis. Blood. 2002; 99:4326-4335; U Bacher, Haferlach C, W Kern, et al. Prognostic relevance of FLT3-TKD mutations in AML: the combination matters—an analysis of 3082 patients. Blood. 2008; 111:2527-2537. Although less frequent than FLT3-ITD and FLT3-TKD mutations, the presence of both FLT3-ITD and FLT3-TKD mutations predicts for the highest rate of relapse and shortest overall survival. Dual mutations occur in approximately 2% of adult acute myeloid leukemia patients. See Schlenk et al. Mutations and treatment outcome in cytogenetically normal acute myeloid leukemia. 2008; 358: 1909-1918.

The heightened frequency of constitutively activated mutant FLT3 in adult AML has made the FLT3 gene a highly attractive drug target in this tumor type. Several FLT3 inhibitors with varying degrees of potency and selectivity for the target have been or are currently being investigated and examined in AML patients. See T Kindler, Lipka D B, and Fischer T. FLT3 as a therapeutic target in AML: still challenging after all these years. Blood. 2010; 116:5089-102.

FLT3 kinase inhibitors known in the art include Lestaurtinib (also known as CEP 701, formerly KT-555, Kyowa Hakko, licensed to Cephalon); CHIR-258 (Chiron Corp.); EB10 and IMC-EB10 (ImClone Systems Inc.); Midostaurin (also known as PKC412, Novartis AG); Tandutinib (also known as MLN-518, formerly CT53518, COR Therapeutics Inc., licensed to Millennium Pharmaceuticals Inc.); Sunitinib (also known as SU11248, Pfizer USA); Quizartinib (also known as AC220, Ambit Biosciences); XL 999 (Exelixis USA, licensed to Symphony Evolution, Inc.); GTP 14564 (Merck Biosciences UK); AG1295 and AG1296; CEP-5214 and CEP-7055 (Cephalon). The following PCT International Applications and U.S. patent applications disclose additional kinase modulators, including modulators of FLT3: WO 2002/032861, WO 2002/092599, WO 2003/035009, WO 2003/024931, WO 2003/037347, WO 2003/057690, WO 2003/099771, WO 2004/005281, WO 2004/016597, WO 2004/018419, WO 2004/039782, WO 2004/043389, WO 2004/046120, WO 2004/058749, WO 2003/024969 and U.S Patent Application No. 2004/0049032. See also Levis M, K F Tse, et al. 2001 "A FLT3 tyrosine kinase inhibitor is selectively cytotoxic to acute myeloid leukemia blasts harboring FLT3 internal tandem duplication mutations." Blood 98(3): 885-887; Tse K F, et al., Inhibition of FLT3-mediated transformation by use of a tyrosine kinase inhibitor. Leukemia. July 2001; 15 (7): 1001-1010; Smith, B. Douglas et al., Singlet agent CEP-701, a novel FLT3 inhibitor, shows biologic and clinical activity in patients with relapsed or refractory acute myeloid leukemia Blood, May 2004; 103: 3669-3676; Griswold, Ian J. et al., Effects of MLN518, A Dual FLT3 and KIT Inhibitor, on Normal and Malignant Hematopoiesis. Blood, November 2004; 104 (9): 2912-2918 [Epub ahead of print July 8]; Yee, Kevin W. H. et al., SU5416 and SU5614 inhibit kinase activity of wild-type and mutant FLT3 receptor tyrosine kinase. Blood, October 2002; 100(8): 2941-2949. O'Farrell, Anne-Marie et al., SU11248 is a novel FLT3 tyrosine kinase inhibitor with potent activity in vitro and in vivo. Blood, May 2003; 101(9): 3597-3605; Stone, R. M et al., PKC-412 FLT3 inhibitor therapy in AML: results of a phase II trials. Ann. Hematol. 2004; 83 Suppl 1:S89-90; and Murata, K. et al., Selective cytotoxic mechanism of GTP-14564, a novel tyrosine kinase inhibitor in leukemia cells expressing a constitutively active Fms-like tyrosine kinase 3 (FLT3). J Biol Chem. Aug. 29, 2003; 278 (35): 32892-32898 [Epub 2003 Jun. 18]; Levis, Mark et al., Small Molecule FLT3 Tyrosine Kinase Inhibitors. Current Pharmaceutical Design, 2004, 10, 1183-1193.

FLT3 inhibitors are classified as Type I or Type II inhibitors. These two classifications are distinguished based on their relative affinities and mechanism of binding to phosphorylated and non-phosphorylated receptor sites. Type I inhibitors recognize the active conformation of kinases. This conformation is conducive to phosphotransfer. Type I inhibitors are generally composed of a heterocyclic ring system. See Liu, Y and N Gray. Rational design of inhibitors that bind to inactive kinase conformations. Nature Chem. Biol. 2006; 2:358-354. Examples of Type I FLT3 inhbitiors include crenolanib and midostaurin. See Muralidhara C, Ramachandran A, Jain V. Crenolanib, a novel type I, mutant-specific inhibitor of class III receptor tyrosine kinases, preferentially binds to phosphorylated kinases. Cancer Research. 2012; 72 (8 Supplement): 3683; J Cools, et al. Prediction of resistance to small molecule FLT3 inhibitors: implications for molecularly targeted therapy of acute leukemia. Cancer Res. 2004; 64:6385-6389. Resistant mutations that render the kinase of the receptor tyrosine kinase constitutively phosphorylated could potentially be sensitive to type I inhibitors that have greater affinity for the phosphorylated kinase.

Type II inhibitors bind preferentially to the inactive conformation of kinases. This conformation is typically referred to as 'DFG-out' owing to the rearrangement of the motif. See J Zhang, Yang PL, and Gray NS. Targeting cancer with small molecule kinase inhibitors. Nature Reviews Cancer. 2009; 9:28-39. Inhibitors such as imatinib, sorafenib and nilotinib bind in the type II conformation. See P W Manley, Cowan-Jacob S W, Mestan J. Advances in the structural biology, design and clinical development of Bcr-Abl kinase inhibitors for the treatment of chronic myeloid leukemia. Biochim. Biophis. Acta. 2005; 1754:3-13; PT Wan, et al. Mechanism of activation of the RAF-ERK signaling pathway by oncogenic mutations of B-RAF. Cell. 2004; 116:855-867. Resistant mutations to Type II inhibitors render the kinase domain of the receptor tyrosine kinase constitutively phosphorylated. Type I inhibitors that target the phosphorylated kinase can overcome the resistance resulting from the treatment with Type II inhibitors, and therefore have potential use in treating diseases that harbor these resistance mutations.

SUMMARY OF THE INVENTION

The present invention includes a method of inhibiting or reducing FLT3 tyrosine kinase activity or expression in a cell or subject with a proliferative disease which comprises administering to the subject having or suspected to have the proliferative disease, a therapeutically or prophylactically effective amount of the compound (hereinafter CP-673,451) of Formula I:

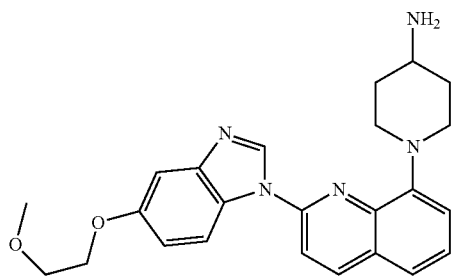 [SMILES: COCCOc1ccc2c(c1)ncn2-c1ccc2cccc(N3CCC(N)CC3)c2n1]

or a pharmaceutically acceptable salt or solvate thereof. In one aspect, the proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the compound is administered at least one of continuously, intermittently, systemically, or locally. In another aspect, the deregulated FLT3 is defined further as a mutated FLT3 is constitutively active. In another aspect, the compound is administered orally, intravenously, or intraperitoneally. In another aspect, CP-673, 451 is a besylate, phosphate, lactate, hydrochloride, citrate, acetate, toluenesulphonate (tosylate) or succinate salt. In another aspect, the FLT3 is at least one of FLT3 ITD, FLT3 D835H, FLT3D835V, FLT3D835Y, FLT3K663Q, FLT3N841I, FLT3R834Q, Dual FLT3 ITD/D835V, or Dual FLT3ITD/F691I I. In another aspect, the therapeutically or prophylactically effective amount of the compound is administered for as long as the subject is in need of treatment for the proliferative disease. In another aspect, the composition is provided at least one of sequentially or concomitantly, with another pharmaceutical agent in a newly diagnosed proliferative disease subject, to maintain remission, or a relapsed/refractory proliferative disease subject. In another aspect, the compound is provided as a single agent or in combination with another pharmaceutical agent in a newly diagnosed proliferative disease subject, to maintain remission, or a relapsed/refractory proliferative disease subject. In another aspect, the compound is provided as a single agent or in combination with another pharmaceutical agent in a newly diagnosed proliferative disease pediatric subject, to maintain remission, or a relapsed/refractory proliferative disease pediatric subject. In another aspect, the subject is relapsed/refractory to prior FLT3 tyrosine kinase inhibition. In another aspect, the further comprises the step of determining if the subject is relapsed/refractory to a prior FLT3 tyrosine kinase inhibitor prior to providing the subject with treatment.

In another embodiment, the present invention includes a method for treating a subject with a proliferative disease comprising: administering to the subject in need of such treatment a therapeutically effective amount of CP-673,451 or a salt thereof, wherein the cell proliferative disorder is characterized by deregulated FLT3 receptor tyrosine kinase activity, proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In one aspect, the compound is administered orally, intravenously, or intraperitoneally. In another aspect, CP-673,451 is a Besylate, Phosphate, Lactate, Hydrochloride, Citrate, Acetate, Toluenesulphonate (tosylate) or Succinate salt. In another aspect, the FLT3 is at least one of FLT3 ITD, FLT3 D835H, FLT3D835V, FLT3D835Y, FLT3K663Q, FLT3N841I, FLT3R834Q, Dual FLT3 ITD/D835V, or Dual FLT3ITD/F691I I. In another aspect, CP-673,451 is provided at least one of sequentially or concomitantly, with chemotherapy, radiotherapy, or surgery in a newly diagnosed proliferative disease, to maintain remission, or a relapsed/refractory proliferative disease. In another aspect, CP-673,451 is provided as a single agent or in combination with chemotherapy, radiotherapy or surgery for treatment of a pediatric subject with the proliferative disease. In another aspect, CP-673,451 is provided as a single agent to at least one of post standard induction therapy, or high dose induction therapy, in newly diagnosed proliferative disease. In another aspect, CP-673,45 µs provided as a single agent in treatment of subjects with the proliferative disease that is either refractory to, or has relapsed after, standard or high dose chemotherapy, radiotherapy or surgery. In another aspect, the subject is relapsed/refractory to at least one other tyrosine kinase inhibitor, including but not limited to crenolanib, sorafenib, quizartinib, PLX3397, sunitinib, midostaurin, or lestaurtinib. In one aspect, the method further comprises the step of determining if the subject is relapsed/refractory including, but not limited to, at least one of Sunitinib, Lestaurtinib/CEP-701, Quizartinib/AC220, Tandutinib/MLN-518, Midostaurin/PKC-412, AST-487, or Sorafenib, and then providing the CP-673,451 or a salt thereof.

Yet another embodiment of the present invention includes a method for treating a subject suffering from leukemia comprising: obtaining a sample from the subject suspected of having a leukemia; determining from the subject sample that the subject has a deregulated FLT3 receptor tyrosine kinase; and administering to the subject in need of such treatment a therapeutically effective amount of CP-673,451 or a salt thereof, wherein the leukemia is characterized by deregulated FLT3 receptor tyrosine kinase activity.

Another embodiment of the present invention includes a method for specifically inhibiting a deregulated receptor tyrosine kinase comprising: obtaining a subject sample and determining which receptor tyrosine kinases are deregulated; and administering to a mammal in need of such treatment a therapeutically effective amount of CP-673,451 or a salt thereof, wherein the deregulated receptor tyrosine kinase is a FLT3 receptor tyrosine kinase. In one aspect, the proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the therapeutically and prophylactically effective amounts are from about 15 to 500 mg per day. In another aspect, the compound is administered at least one of continuously, intermittently, systemically, or locally. In another aspect, the deregulated FLT3 is defined further as a mutated FLT3 is constitutively active. In another aspect, the compound is administered orally, intravenously, or intraperitoneally. In another aspect, the CP-673,451 is a Besylate, Phosphate, Lactate, Hydrochloride, Citrate, Acetate, Toluenesulphonate (tosylate) or Succinate salt. In another aspect, the FLT3 is at least one of FLT3 ITD, FLT3 D835H, FLT3D835V, FLT3D835Y, FLT3K663Q, FLT3N841I, FLT3R834Q, Dual FLT3 ITD/D835V, or Dual FLT3ITD/F691I. In another aspect, the therapeutically or prophylactically effective amount of the compound is administered daily for as long as the subject is in need of treatment for the proliferative disease. In one aspect, the subject is provided treatment, one or more subject samples are obtained to determine the effect of the treatment, and treatment is continued until the proliferative disease is reduced or eliminated. In another aspect, the compound is provided at least one of sequentially or concomitantly, with another pharmaceutical agent in a newly diagnosed proliferative disease subject, to maintain remission of an existing subject, or a relapsed/refractory proliferative disease subject. In another aspect, the present invention is provided as a single agent or in combination with another pharmaceutical agent in a newly diagnosed proliferative disease subject, to maintain remission, or a relapsed/refractory proliferative disease subject. In another aspect, the present invention is provided as a single agent or in combination with another pharmaceutical agent in a newly diagnosed proliferative disease pediatric subject, to maintain remission, or a relapsed/refractory proliferative disease pediatric subject. In another aspect, the subject is relapsed/refractory to a prior FLT3 tyrosine kinase inhibitor. In one aspect, the method further comprises the step of determining if the subject is relapsed/refractory including, but not limited to, at least one of Sunitinib, Lestaurtinib/CEP-701, Quizartinib/AC220, Tandutinib/MLN-518, Midostaurin/PKC-412, AST-487, or Sorafenib, and then providing the CP-673,451 or a salt thereof.

Yet another embodiment of the present invention includes a method for treating a subject with cancer comprising:

obtaining a sample suspected of having cancer from the subject; determining if the subject that has become resistant to prior FLT3 protein tyrosine kinase inhibition; and administering a therapeutically effective amount of CP-673,451 or a salt thereof to overcome the resistance to the prior FLT3 protein tyrosine kinase inhibition In one aspect, the method further comprises the step of determining if the subject is relapsed/refractory including, but not limited to, at least one of Sunitinib, Lestaurtinib/CEP-701, Quizartinib/AC220, Tandutinib/MLN-518, Midostaurin/PKC-412, AST-487, or Sorafenib, and then providing the CP-673,451 or a salt thereof.

The present invention provides methods of reducing or inhibiting the kinase activity of FLT3 in a cell or a subject, and the use of such methods for preventing or treating cell proliferative disorder (s) related to FLT3. Other features and advantages of the invention will be apparent from the following detailed description of the invention and from the claims.

BRIEF DESCRIPTION OF THE DRAWINGS

For a more complete understanding of the features and advantages of the present invention, reference is now made to the detailed description of the invention along with the accompanying figure in which:

(FIG. 1A): shows replicates of a first (left) and a second (right) standard dose-response curve for the non-autoinhibited state of FLT3; (FIG. 1B): shows replicates of a first (left) and a second (right) standard dose-response curve for the autoinhibited state of FLT3. The amount of kinase measured by qPCR (signal; y-axis) is plotted against the corresponding CP-673,451 concentration in nanomolar in log 10 scale (x-axis). Data points marked with an "x" were not used for Kd determination.

DETAILED DESCRIPTION OF THE INVENTION

Figure 1A:
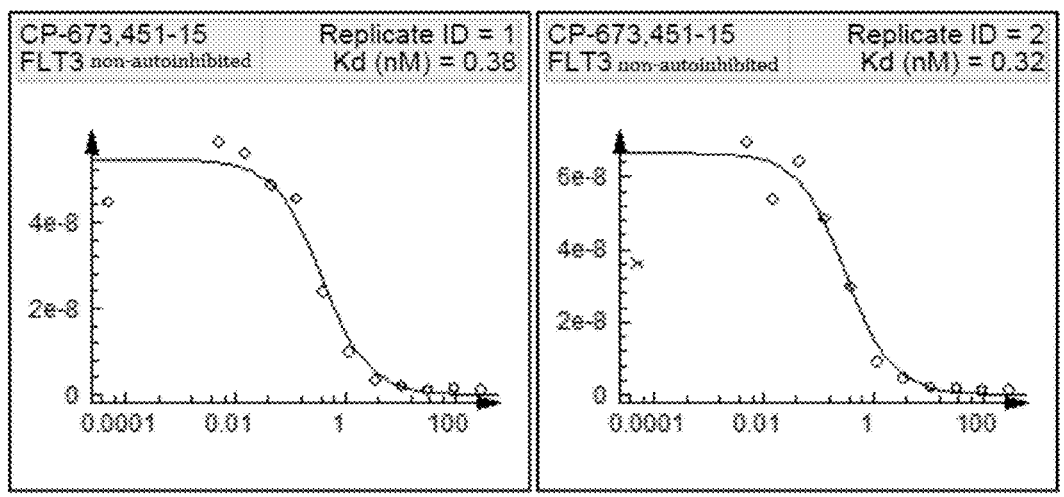
FIGS. 1A and 1B show the affinity of the tosylate salt of the present invention for the non-autoinhibited and autoinhibited states of FLT3.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention comprises the use of the compounds of the present invention to inhibit FLT3 kinase activity in a cell or a subject, or to treat disorders related to FLT3 kinase activity or expression in a subject.

In one embodiment to this aspect, the present invention provides a method for reducing or inhibiting the kinase activity of FLT3 in a cell comprising the step of contacting the cell with a compound of the present invention. The present invention also provides a method for reducing or inhibiting the kinase activity of FLT3 in a subject comprising the step of administering a compound of the present invention to the subject. The present invention further provides a method of inhibiting cell proliferation in a cell comprising the step of contacting the cell with a compound of the present invention.

The term "subject" refers to an animal, such as a mammal or a human, who has been the object of treatment, observation or experiment.

The term "contacting" refers to the addition of the present invention or pharmaceutically acceptable salt to cells such that the compound is taken up by the cell.

In other embodiments to this aspect, the present invention provides both prophylactic and therapeutic methods for treating a subject at risk or susceptible to developing a cell proliferative disorder driven by aberrant kinase activity of FLT3. In one example, the invention provides methods for preventing a cell proliferative disorder related to FLT3, comprising administration of a prophylactically effective amount of a pharmaceutical composition comprising a compound of the present invention in a subject. Administration of said prophylactic agent can occur prior to the manifestation of symptoms characteristic of the FLT3 driven cell proliferative disorder, such that a disease or disorder is prevented or, alternatively, delayed in its progression. Non-limiting examples of FLT3 mutants that can be targeted or tested using the present invention include, e.g., FLT3 ITD, FLT3 D835H, FLT3D835V, FLT3D835Y, FLT3K663Q, FLT3N841I, FLT3R834Q, Dual FLT3 ITD/D835V, and/or Dual FLT3ITD/F691I.

The term "prophylactically effective amount" refers to an amount of active compound or pharmaceutical salt that inhibits or delays in a subject the onset of a disorder as being sought by a researcher, veterinarian, medical doctor or other clinician.

The term "therapeutically effective amount" as used herein, refers to an amount of active compound or pharmaceutical salt that elicits the biological or medicinal response in a subject that is being sought by a researcher, veterinarian, medical doctor or other clinician, which includes alleviation of the symptoms of the disease or disorder being treated.

Methods for determining therapeutically and prophylactically effective doses for pharmaceutical compositions comprising a compound of the present invention are known in the art.

As used herein, the term "composition" refers to encompass a product comprising the specified ingredients in the specified amounts, e.g., CP-673,451, as well as any product which results, directly or indirectly, from combinations of the specified ingredients in the specified amounts.

As used herein, the terms "disorder related to FLT3," or "disorders related to FLT3 receptor," or "disorders related to FLT3 receptor tyrosine kinase," or "FLT3 driven cell proliferative disorder" includes diseases associated with or implicating FLT3 activity, for example, mutations leading to constitutive activation of FLT3. Examples of "disorders related to FLT3" include disorders resulting from over stimulation of FLT3 due to mutations in FLT3, or disorders resulting from abnormally high amount of FLT3 activity due to abnormally high amount of mutations in FLT3. It is known that over-activity of FLT3 has been implicated in the pathogenesis of many diseases, including the following listed cell proliferative disorders, neoplastic disorders and cancers.

The term "cell proliferative disorders" refers to excess cell proliferation of one or more subset of cells in a multicellular organism resulting in harm (i.e. discomfort or decreased life expectancy) to the multicellular organism. Cell proliferative disorders can occur in different types of animals and humans. As used herein, "cell proliferative disorders" include neoplastic disorders.

The term "neoplastic disorder" as used herein, refers to a tumor resulting from abnormal or uncontrolled cellular growth. Examples of neoplastic disorders include, but are not limited to the following disorders, for instance: the myeloproliferative disorders, such as thrombocytopenia, essential thrombocytosis (ET), agnogenic myeloid metaplasia, myelofibrosis (MF), myelofibrosis with myeloid metaplasia (MMM), chronic idiopathic myelofibrosis (UIMF), and polycythemia vera (PV), the cytopenias, and pre-malignant myelodysplastic syndromes; cancers such as glioma cancers, lung cancers, breast cancers, colorectal cancers, prostate cancers, gastric cancers, esophageal cancers, colon cancers, pancreatic cancers, ovarian cancers, and hematological malignancies, including myelodysplasia, multiple myeloma, leukemias, and lymphomas. Examples of hematological malignancies include, for instance, leukemias, lymphomas, Hodgkin's disease, and myeloma. Also, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML, with trilineage myelodysplasia (AMLITMDS), mixed lineage leukemia (MLL), myelodysplastic syndromes (MDSs), myeloproliferative disorders (MPD), and multiple myeloma (MM). The present invention can be used to overcome resistance to one or more chemotherapies to which the above cancers have become relapsed/refractory including, but not limited to, at least one of Sunitinib, Lestaurtinib/CEP-701, Quizartinib/AC220, Tandutinib/MLN-518, Midostaurin/PKC-412, AST-487, or Sorafenib, and then providing the CP-673,451 or a salt thereof.

In a further embodiment, the present invention can be combined with another therapy as a combination therapy for treating or inhibiting the onset of a cell proliferative disorder related to FLT3 in a subject. The combination therapy comprises the administration of a prophylactically and therapeutically effective amount of a compound of the present invention and one or more other anti-cell proliferation therapies including, but not limited to, chemotherapy and radiation therapy.

In an embodiment of the present invention, a compound of the present invention may be administered in combination with chemotherapy. As used herein, the term "chemotherapy" refers to a therapy involving a chemotherapeutic agent. A variety of chemotherapeutic agents may be used in combination with the present invention. By way of example only, taxane compounds, specifically docetaxel, is safely administered in combination with a compound of the present invention in a dosage of 75 mg per square meter (mg/m$^2$) of body surface area. The appropriate dosage and scheme for chemotherapy will be similar to those already employed in clinical therapies wherein the chemotherapy is delivered in combination with other therapies or used alone.

In another embodiment of the present invention, compounds of the present invention may be administered in combination with radiation therapy. As used herein, the term "radiation therapy" refers to a therapy that comprises the exposure of a subject in need to radiation. Radiation therapy is known to those skilled in the art. The appropriate dosage and scheme for radiation therapy will be similar to those already employed in clinical therapies wherein the radiation therapy is delivered in combination with other therapies or used alone.

In another embodiment of the present invention, the compounds of the present invention may be administered in combination with a targeted therapy. As used herein, the term "targeted therapy" refers to a therapy targeting a particular class of proteins involved in tumor development or oncogenic signaling. For example, tyrosine kinase inhibitors against vascular endothelial growth factor have been used in treating cancers.

The present invention also includes methods that include the use of a second pharmaceutical agent in addition to compounds of the present invention, the two may be administered simultaneously or sequentially (in either order).

In one embodiment, the present invention therapeutically effective amounts of the compound (CP-673,451) having formula I:

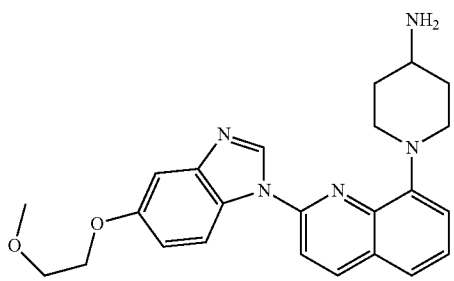 [SMILES: COCCOc1ccc2c(c1)ncn2-c1ccc2cccc(N3CCC(N)CC3)c2n1]

or a pharmaceutically acceptable salt or solvate thereof, in a therapeutically or prophylactically effective amount against a proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. Pharmaceutically acceptable salts including hydrochloride, phosphate and lactate are prepared in a manner similar to the benzenesulfonate salt and are well known to those of moderate skill in the art.

Compounds of the present invention may be administered to a subject systemically, for example, orally, intravenously, subcutaneously, intramuscular, intradermal or parenterally. The compounds of the present invention can also be administered to a subject locally.

Compounds of the present invention may be formulated for slow-release or fast-release with the objective of maintaining contact of compounds of the present invention with targeted tissues for a desired range of time.

Compositions suitable for oral administration include solid forms, such as pills, tablets, caplets, capsules, granules, and powders, liquid forms, such as solutions, emulsions, and suspensions. Forms useful for parenteral administration include sterile solutions, emulsions and suspensions.

The compounds of the present invention may be administered on a daily regimen, once, twice, three or more times per day. Optimal doses to be administered may be determined by those skilled in the art, and will vary with the compound of the present invention used, the mode of administration, the time of administration, the strength of the preparation, the details of the disease condition. One or more factors associated with subject characteristics, such as age, weight, and diet will call for dosage adjustments. Techniques and compositions for making useful dosage forms using the CP-673,451 are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); relevant portions incorporated herein by reference.

A dosage unit for use of CP-673,451, may be a single compound or mixtures thereof with other compounds, e.g., a potentiator. The compounds may be mixed together, form ionic or even covalent bonds. The compounds of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the compounds of the present invention to a patient in need of therapy that includes the compound of Formula I.

CP-673,451 can be administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, CP-673,451 may be formulated to provide, e.g., maximum and/or consistent dosing for the particular form for oral, rectal, topical, intravenous injection or parenteral administration. While CP-673,451 may be administered alone, it will generally be provided in a stable salt form mixed with a pharmaceutically acceptable carrier. The carrier may be solid or liquid, depending on the type and/or location of administration selected.

Preparation of the compounds of the present invention. General synthetic methods which may be referred to for preparing the compounds of formula I are provided in U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application No. US 2005/0124599 (Pfizer, Inc.) and U.S. Pat. No. 7,183,414 (Pfizer, Inc.), relevant portions incorporated herein by reference.

Pharmaceutically acceptable salts such as hydrochloride, phosphate and lactate are prepared in a manner similar to the benzenesulfonate salt and are well known to those of moderate skill in the art. The following representative compound of the present invention are for exemplary purposes only and are in no way meant to limit the invention, including CP-673,451 as a Besylate, Phosphate, Lactate, Hydrochloride, Citrate, Acetate, Toluenesulphonate and Succinate salt.

Biological Activity.

In Vitro Assays. The following representative in vitro assays were performed in determining the FLT3 biological activity of the present invention. These are given to illustrate the invention in a non-limiting fashion.

Inhibition of wild type and mutated FLT3 enzyme activity and specificity for the inhibition of the phosphorylated form of FLT3 exemplify the specific inhibition of the FLT3 enzyme and cellular processes that are dependent on FLT3 activity. All of the examples herein show significant and specific inhibition of the FLT3 kinase and FLT3-dependent cellular responses.

Competitive binding assay. Inhibition of the kinase domain of the human FLT3 receptor was performed using the KINOMEscan KdElect assay protocol. The KINOMEscan platform utilizes a high-throughput competitive binding technology. The assay was performed by combining DNA-tagged kinase, immobilized ligand, and the present invention. The ability of the present invention to compete with immobilized ligand was measured using quantitative PCR of the DNA tag. The competition binding assay was used to evaluate the present invention against a panel of 96 human protein kinases.

Kinase-tagged T7 phage strains were grown in parallel in 24-well blocks in an *E. coli* host derived from the BL21 strain. *E. coli* were grown to log phase and infected with T7 phage from a frozen stock and incubated with shaking at 32 degrees Celsius until lysis. The lysates were then centrifuged and filtered. The remaining kinases were produced in HEK-293 cells and tagged with DNA for quantitative PCR detection. Affinity resins for the kinase assay were generated by treating streptavidin-coated magnetic beads with biotinylated small molecule ligands for 30 minutes at room temperature. The liganded beads were blocked with excess biotin and washed with blocking buffer consisting of Sea Block, 1% Bovine Serum Albumin (BSA) 0.05% Tween 20, 1 mM Dithithreitol (DTT) in order to reduce non-specific phage binding. An 11-point 3-fold serial dilution of the present invention was prepared as a 40× stock in 100% Dimethyl sulfoxide (DMSO) and diluted to 1× directly into the assay.

Binding reactions were initiated by combining the liganded affinity beads, kinases, and the present invention in 1× binding buffer consisting of 20% Sea Block, 0.17 Phosphate Buffered Saline (PBS), 0.05% Tween 20, 6 mM DTT. All reactions were performed in polypropylene 384-well plates in a final volume of 0.04 mL. The plates were incubated for 1 hour while shaking at room temperature. The affinity beads were washed with 1×PBS and 0.05% Tween 20 buffer, then re-suspended in elution buffer consisting of 1×PBS, 0.05% Tween 20, 0.5 uM non-biotinylated affinity ligand. Following re-suspension, the affinity beads were incubated at room temperature with shaking. The elutant kinase concentration was then measured by quantitative PCR.

Binding constants (Kds) were calculated with a standard dose-response curve using the Hill equation. Curves were fitted using a non-linear least square fit with the Levenberg-Marquardt algorithm. Kds of the present invention were compared to both a negative DMSO control and a positive control compound. The binding affinity of the present invention was visualized using the compound profile visualization interaction map, TREEspot.

Direct enzyme phosphorylation assay. The Millipore Kinase IC50 Profiler assay was used to screen the present invention against a panel of normal FLT3 and mutated FLT3 kinases. For assays of both kinases, the FLT3 enzyme was incubated with 8 mM of 3-(N-morpholino)propanesulfonic acid (MOPS) at a pH of 7.0, 0.2 mM Ethylenediaminetetraacetic acid (EDTA), 50 uM, a synthetic Abl peptide substrate EAIYAAPFAKKK (SEQ ID NO: 1), 10 mM MgAcetate and [γ-$^{33}$P-ATP]. The reaction was initiated by the addition of MgATp mix. The reaction mixture was incubated for 40 minutes at room temperature and halted by the addition of 3% phosphoric acid solution. 10 uL of the reaction solution was spotted on P30 filtermat and washed three times in 75 mM phosphoric acid for 5 minutes and then once in methanol prior to drying and scintillation counting. The scintillation values for each replicate, including positive and negative controls, were analyzed using XLFit version 5.1 to determine the IC50 values for the present invention against normal and mutated FLT3.

Biological data for non-autoinhibited, constitutively active kinase affinity.

Figure 1B:
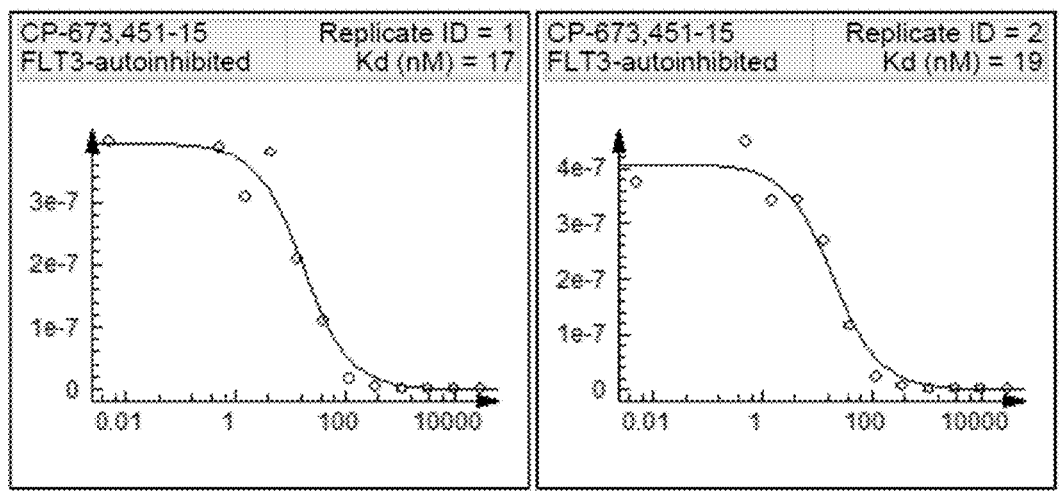

The difference in binding affinities of the tosylate salt of the present invention for the non-autoinhibited and autoinhibited states of FLT3 indicate that the molecule functions as a type I inhibitor. As shown in FIGS. 1A, 1B and Table 1, the tosylate salt of the present invention has an average Kd value of 0.35 nM for non-autoinhibited FLT3 and 18 nM for autoinhibited FLT3. The tosylate salt of the present invention thus has an approximately 50-fold affinity shift between the non-autoinhibited and autoinhibited states of FLT3. This value is within the range of affinity shifts reported for other type I tyrosine kinase inhibitors and is far outside the range of affinity shifts reported for type II TKIs. See Davis, M I et al., Comprehensive analysis of kinase inhibitor selectivity. Nat Biotechnology. 2011; 29 (10): 1046-1051; Zhang, J et al., Targeting cancer with small molecule kinase inhibitors. Nat Rev Cancer. 2009; 9(1): 28-39; Liu, Y et al., Rational design of inhibitors that bind to inactive kinase conformations. Nat Chem Biol. 2006; 2(7): 358-364.

TABLE 1

CP-673,451 is a type I TKI with increased affinity for non-autoinhibited constitutively active FLT3.

| Kinase Target | Binding Constant (Kd) |
|---|---|
| FLT3 non-autoinhibited | 0.35 nM |
| FLT3 autoinhibited | 18 nM |

Biological Data for Wild Type FLT3.

The tosylate salt of CP-673,451 tightly binds the FLT3 receptor. The binding affinity(Kd) of the present invention for wild type FLT3 is compared to that of other known FLT3 inhibitors in the art (Table 2). All binding constants are presented in nanomolar concentration. The Kd of the tosylate salt of the present invention for wild type FLT3 is 0.35 nM. The affinity of the present invention is the highest for wild type FLT3 when compared to a number of other FLT3 TKIs known in the art.

TABLE 2

Binding constants (Kd) of the tosylate salt of the present invention compared to other FLT3 TKIs known in the art for wild type FLT3.

| RTK | Compound | Binding Constant (Kd) |
|---|---|---|
| FLT3 wild type | CP-673,451 | 0.35 nM |
| | AST-487 | 0.79 M |
| | Quizartinib/AC220 | 1.3 nM |
| | Tandutinib/MLN-518 | 3 nM |
| | Lestaurtinib/CEP-701 | 8.5 nM |
| | Midostaurin/PKC-412 | 13 nM |

Figure 2:
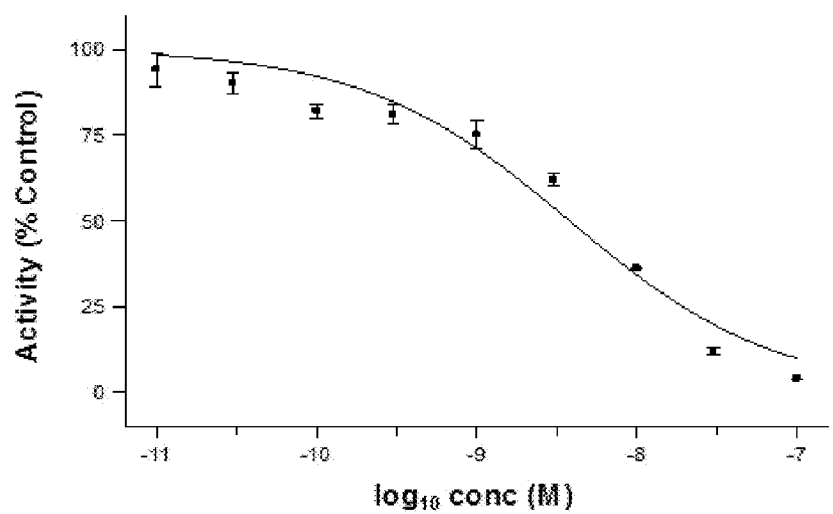
FIG. 2 shows the dose-response curve (n=2) for IC50 determination of the tosylate salt of the present invention for wild-type FLT3. The activity of the tosylate salt of CP-673,451 is plotted against the corresponding molar concentration in log 10 scale.

The activity of the tosylate salt of the present invention for FLT3 wild type was determined using a direct enzymatic Millipore IC50 profiler assay. In the direct enzymatic measurement assay, the IC50 of the tosylate salt of the current invention against wild type FLT3 was 4 nM (FIG. 2).

Biological Data for the FLT3-ITD Mutation.

Figure 3:
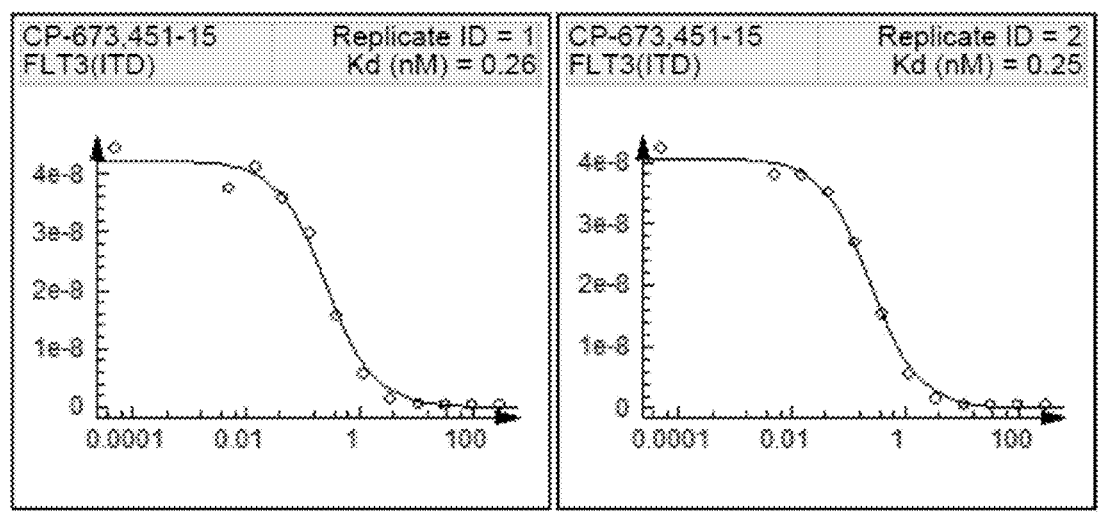
FIG. 3 shows replicates of a first (left) and a second (right) standard dose-response curve for Kd determination of the tosylate salt of the present invention for FLT3 ITD. The amount of kinase measured by qPCR (signal; y-axis) is plotted against the corresponding CP-673,451 concentration in nanomolar in log 10 scale (x-axis).

The affinity of the tosylate salt of the present invention for FLT3 with an ITD mutation is presented in Table 3. All binding constants are presented in nanomolar concentration. The Kd of the tosylate salt of the present invention for FLT3-ITD is 0.25 nM (FIG. 3). The affinity of the tosylate salt of the present invention is the highest for mutant FLT3-ITD when compared to a number of other FLT3 TKIs inhibitors known in the art.

TABLE 3

Binding constants (Kd) of the tosylate salt of the present invention compared to other FLT3 TKIs known in the art for FLT3-ITD.

| RTK | Compound | Binding Constant (Kd) |
|---|---|---|
| FLT3 ITD | CP-673,451 | 0.25 nM |
| | Sunitinib | 0.99 nM |
| | Lestaurtinib/CEP-701 | 1.5 nM |
| | Quizartinib/AC220 | 8.8 nM |
| | Tandutinib/MLN-518 | 9.1 nM |
| | Midostaurin/PKC-412 | 11 nM |
| | AST-487 | 11 nM |
| | Sorafenib | 79 nM |

Biological data for the FLT3-TKD mutation.

Figure 4A:
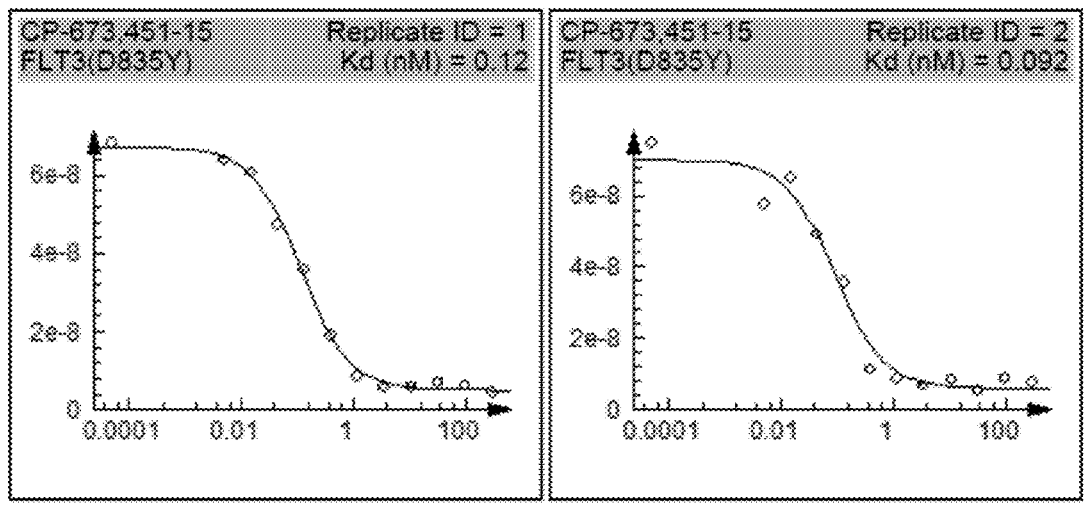
FIGS. 4A, 4B, and 4C show the replicates of standard dose-response curves for Kd determination of the tosylate salt of the present invention for (FIG. 4A) replicates of a first (left) and a second (right) for FLT3 D835Y, (FIG. 4B) replicates of a first (left) and a second (right) FLT3 D835H, and (FIG. 4C) replicates of a first (left) and a second (right) FLT3 D835V. The amount of kinase measured by qPCR (signal; y-axis) is plotted against the corresponding CP-673, 451 concentration in nanomolar in log 10 scale (x-axis). Data points marked with an "x" were not used for Kd determination.
Figure 4B:
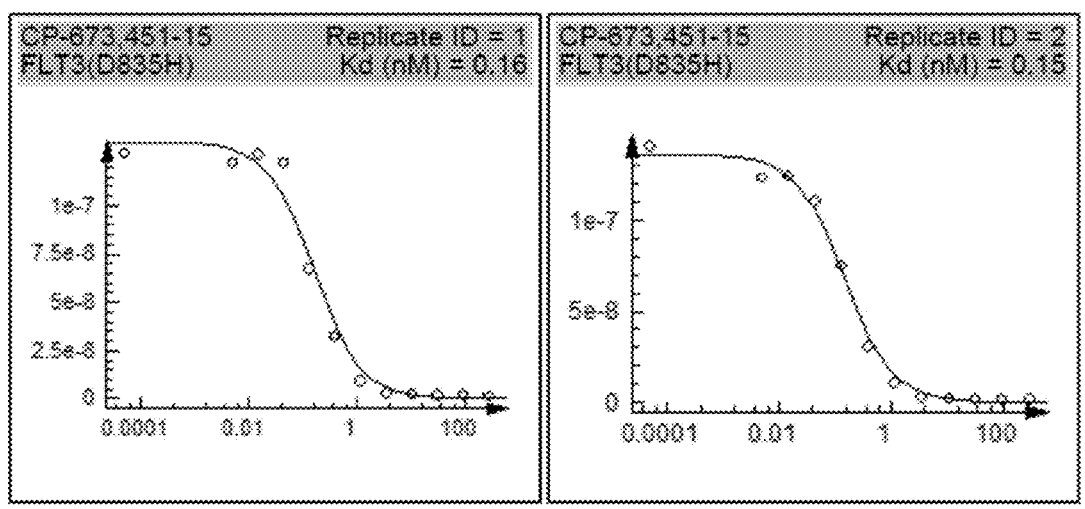
Figure 4C:
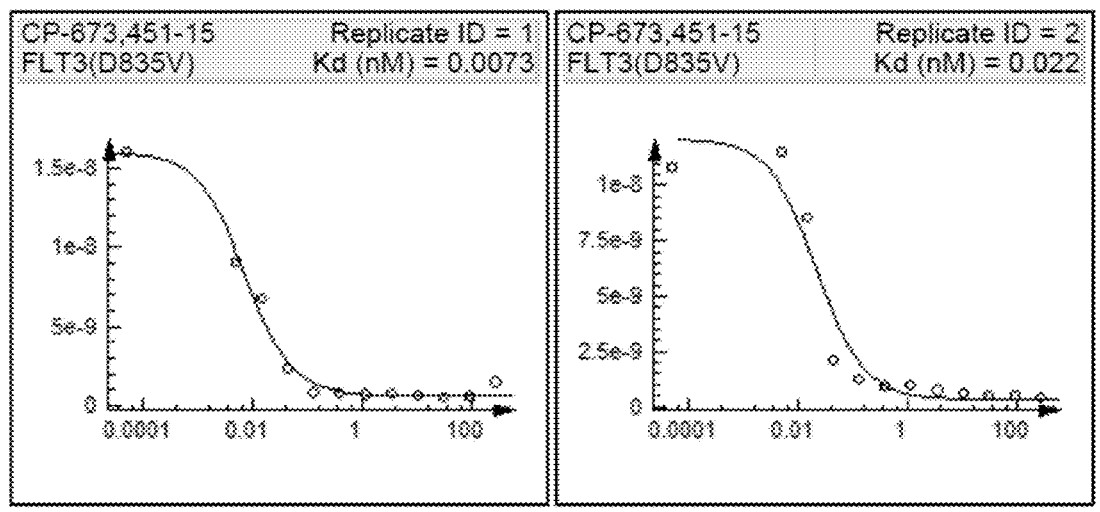

The tosylate salt of the present invention has a heightened binding affinity for the FLT3 tyrosine kinase domain mutations D835Y, D835H, and D835V. The Kd of the tosylate salt of the present invention for the FLT3 D835Y, D835H, and D835V mutations is 0.10 nM, 0.16 nM, and 0.015 nM respectively (FIGS. 4A, 4B, and 4C, respectively). The Kd of the tosylate salt of CP-673,451 for FLT3 tyrosine kinase domain mutations K663Q, N841I, and R834Q is 0.62 nM, 0.39 nM, and 0.65 nM, respectively (Table 4).

TABLE 4

Binding constants (Kd) of the tosylate salt of CP-673,451 for FLT3 TKD mutations K663Q, N841I, and R834Q.

| FLT3 TKD mutation | Binding Constant (Kd) |
| --- | --- |
| FLT3 N841I | 0.39 nM |
| FLT3 K663Q | 0.62 nM |
| FLT3 R834Q | 0.65 nM |

Figure 5:
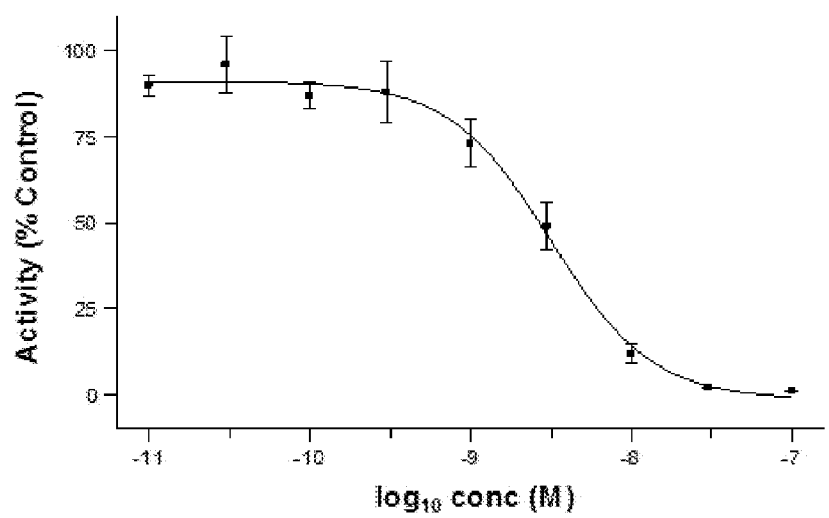
FIG. 5 shows the dose-response curve (n=2) for IC50 determination of the tosylate salt of the present invention for FLT3 D835Y. The activity of the tosylate salt of CP-673,451 is plotted against the corresponding molar concentration in log 10 scale.

The activity of the tosylate salt of the present invention was determined using a direct enzymatic Millipore IC50 profiler assay. In the direct enzymatic measurement assay, the IC50 of the tosylate salt of the current invention against the FLT3 TKD mutation D835Y was 3 nM (FIG. 5).

Biological data for the dual FLT3 (ITD,TKD) mutations.

Figure 6A:
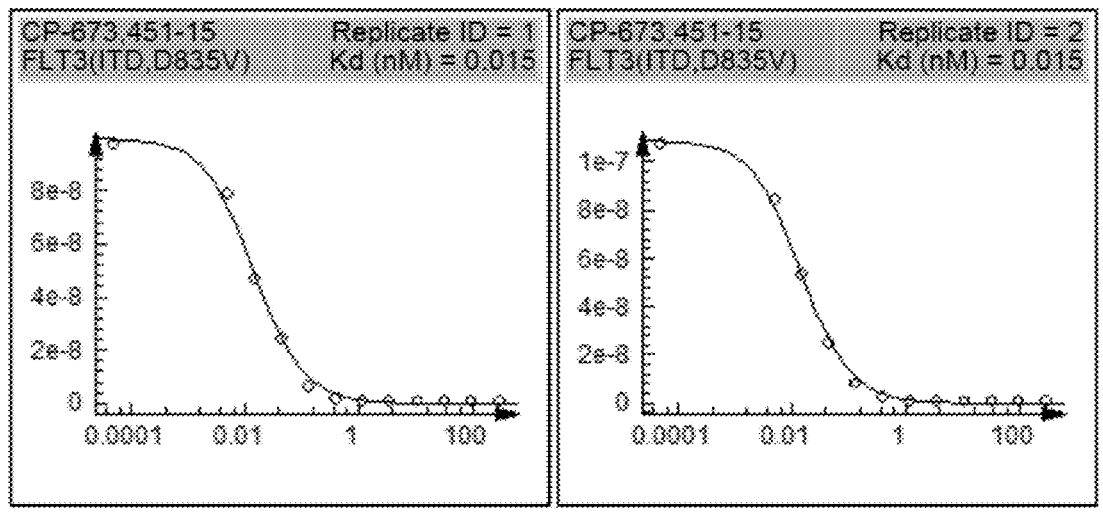
FIGS. 6A and 6B show the replicates of standard dose-response curves for Kd determination of the tosylate salt of the present invention for (FIG. 6A) replicates of a first (left) and a second (right) for dual mutant FLT3 (ITD,D835V), (FIG. 6B) replicates of a first (left) and a second (right) for dual mutant FLT3 (ITD,F691I). the amount of kinase measured by qPCR (signal; y-axis) is plotted against the corresponding CP-673,451 concentration in nanomolar in log 10 scale (x-axis).
Figure 6B:
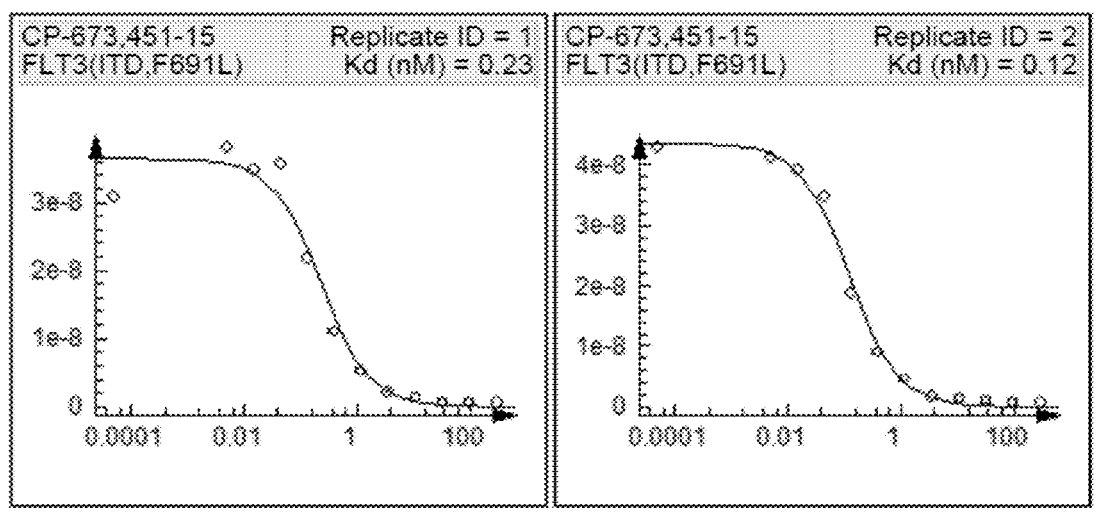

The tosylate (toluenesulfonate) salt of the present invention has a heightened binding affinity for dual FLT3 (ITD, TKD) mutations. The Kd of the tosylate salt of the present invention for the FLT3 (ITD, D835V) and FLT3 (ITD, F691I) double mutants is 0.015 nM and 0.18 nM, respectively (FIGS. 6A and 6B, respectively).

The biological activity of the tosylate salt of the present invention was used to evaluate activity against the FLT3-ITD mutation, dual FLT3-ITD/FLT3-D835 mutation, using Type I FLT3 TKI,CP-673,451, to overcome resistance associated with a Type II FLT3 TKI.

Biological Data for the FLT3-ITD Mutation.

The ability of the tosylate (toluenesulfonate) salt of CP-673,451 to inhibit phosphorylated FLT3 was determined using cell lines expressing FLT3-ITD, including Molm-13 (a human acute myeloid leukemia cell line) and BaF3 (bone marrow-derived pro-B-cell line) cells transduced to express FLT3. The effect was examined by western blot. It was found that CP-673,451 inhibited the phosphorylation of the FLT3-ITD receptor in the cell lines at nanomolar IC50 concentrations of 0.7 nM and 5.1 nM, respectively (Table 5).

TABLE 5

Potency of the tosylate salt of CP-673,451 against FLT3-ITD as measured by phosphorylation inhibition in FLT3-ITD cell lines Molm 13 and Ba/F3.

| RTK | Cell Line | IC50 |
| --- | --- | --- |
| FLT3-ITD | Molm 13 | 0.7 nM |
|  | Ba/F3 FLT3-ITD | 5.1 nM |

Biological Data for FLT3-ITD/FLT3-D835 Mutation.

The activity of CP-673,451 was tested against Ba/F3 cells with a FLT3-ITD and FLT3-D835Y mutation. CP-673,451 potently decreased the viability of Ba/F3 expressing FLT3-D835Y/ITD cells with an IC50 value of 23.8 nM (Table 6). The sensitivity of CP-673,451 was superior to that of AC220 treatment for Ba/F3 FLT3-D835Y/ITD expressing cells.

TABLE 6

Potency of the tosylate salt of the present invention compared to AC220, another FLT3 TKI known in the art, in Ba/F3 cells with a double FLT3 ITD/FLT3-D835Y mutation.

| Cell line | CP-7673,451 pFLT3 | AC220 IC50 pFLT3 |
| --- | --- | --- |
| Ba/F3 FLT-ITD/D835Y | 23.8 nM | 93.1 nM |

Biological Data using the Type I FLT3 TKI, CP-673,451, to Overcome Resistance Associated with a Type II FLT3 TKI.

The ability of CP-673,451 to overcome prior FLT3 TKI resistance was determined via MTT assay using Molm 13-RES-luc cells that expressed FLT3-ITD/D835Y generated by continuous treatment with the FLT3 inhibitor tandutinib. The effect of the tosylate salt of CP-673,451 was determined in tandutinib-resistant Molm 13 cells harboring the dual FLT3-ITD/D835Y mutation. It was found that CP-673,451 significantly decreased tandutinib-resistant Molm 13 cell viability with a mean IC50 value of 3.3. nM (Table 7) from 3 separate studies with 6 replicates each (n=18).

TABLE 7

Potency of the tosylate salt of the present invention against FLT3 TKI tandutinib resistant Molm 13 cells harbouring a dual FLT3-ITD/D835Y mutation.

| Cell Line | Cell line mutation profile | Crenolanib IC50 pFLT3 |
| --- | --- | --- |
| Tandutinib resistant Molm 13 | FLT3-ITD/D835Y | 3.3 nM |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Cancer Genome Atlas Research Network. Genomic and epigenetic landscapes of adult de novo acute myeloid leukemia. N Eng J Med. 2013; 388: 2059-74.
Patel, J P et al. Prognostic relevance of integrated genetic profiling in acute myeloid leukemia. N Eng J Med. 2012; 366:1079-1089.
Muralidhara C, Ramachandran A, Jain V. Crenolanib, a novel type I, mutant-specific inhibitor of class III receptor tyrosine kinases, preferentially binds to phosphorylated kinases. Cancer Research. 2012; 72 (8 Supplement): 3683.
Drexler, H G et al. Expression of FLT3 receptor and response to FLT3 ligand by leukemic cells. Leukemia. 1996; 10:588-599.
Gilliland, D G and J D Griffin. The roles of FLT3 in hematopoiesis and leukemia. Blood. 2002; 100:1532-1542.
Stirewalt, D L and J P Radich. The role of FLT3 in hematopoietic malignancies. Nat Rev Cancer. 2003; 3:650-665.
Nakao M, S Yokota and T Iwai. Internal tandem duplication of the FLT3 gene found in acute myeloid leukemia. Leukemia. 1996; 10:1911-1918.
H Kiyoi, M Towatari and S Yokota. Internal Tandem duplication of the FLT3 gene is a novel modality of elongation mutation which causes constitutive activation of the product. Leukemia. 1998; 12:1333-1337.
P D Kottaridis, R E Gale, et al. The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials. Blood. 2001; 98: 1742-1759.
Yamamoto Y, Kiyoi H, Nakano Y. Activating mutation of D835 within the activation loop of FLT3 in human hematologic malignancies. Blood. 2001; 97:2434-2439.
Thiede C, C Steudel, Mohr B. Analysis of FLT3-activating mutations in 979 patients with acute myelogenous leukemia: association with FAB subtypes and identification of subgroups with poor prognosis. Blood. 2002; 99:4326-4335.
S Bains, Luthra R, Medeiros L J and Zuo Z. FLT3 and NPM1 mutations in myelodysplastic syndromes: Frequency and potential value for predicting progression to acute myeloid leukemia. American Journal of Clinical Pathology. January 2011; 135:62-69.
P K Bhamidipati, Daver N G, Kantarjian H, et al. *FLT3* mutations in myelodysplastic syndromes (MDS) and chronic myelomonocytic leukemia (CMML). 2012. *Journal of Clinical Oncology. Suppl; abstract* 6597.
H Kiyoi, M Towatari and S Yokota. Internal Tandem duplication of the FLT3 gene is a novel modality of elongation mutation which causes constitutive activation of the product. Leukemia. 1998; 12: 1333-1337.
H Kiyoi, T Naoe and S Yokota. Internal tandem duplication of FLT3 associated with leukocytosis in acute promyelocytic leukemia. Leukemia Study Group of the Ministry of Health and Welfare (Kohseisho). Leukemia. 1997; 11: 1447-1452.
S Schnittger, C Schoch and M Duga. Analysis of FLT3 length mutations in 1003 patients with acute myeloid leukemia: correlation to cytogenetics, FAB subtype, and prognosis in the AMLCG study and usefulness as a marker for the detection of minimal residual disease. Blood. 2002; 100:59-66.
F M Abu-Duhier, Goodeve A C, Wilson G A, et al. *FLT3* internal tandem duplication mutations in adult acute myeloid leukemia define a high risk group. British Journal of Haematology. 2000; 111:190-195.
H Kiyoi, T Naoe, Y Nakano, et al. Prognostic implication of FLT3 and N-RAS gene mutations in acute myeloid leukemia. Blood. 1999; 93:3074-3080.
D L Stirewalt and J P Radich. The role of FLT3 in haematopoietic malignancies. Nature Reviews Cancer. 2003; 3: 650-665

Y Yamamoto, H Kiyoi and Y Nakano, et al. Activating mutation of D835 within the activation loop of FLT3 in human hematologic malignancies. Blood. 2001; 97:2434-2439.

C Thiede, Steudal C, Mohr B, et al. Analysis of FLT3-activating mutations in 979 patients with acute myelogenous leukemia: association with FAB subtypes and identification of subgroups with poor prognosis. Blood. 2002; 99: 4326-4335.

U Bacher, Haferlach C, W Kern, et al. Prognostic relevance of FLT3-TKD mutations in AML: the combination matters—an analysis of 3082 patients. Blood. 2008; 111: 2527-2537.

T Kindler, Lipka D B, and Fischer T. FLT3 as a therapeutic target in AML: still challenging after all these years. Blood. 2010; 116: 5089-102.

Liu, Y and N Gray. Rational design of inhibitors that bind to inactive kinase conformations. Nature Chem. Biol. 2006; 2:358-354.

A Ramachandran, Marshall H and Jain V. Crenolanib, a novel type I, mutant specific inhibitor of class III receptor tyrosine kinases, preferentially binds to phosphorylated kinases. Cancer Res. 2012; 72 (8 supplement): 3683.

J Zhang, Yang P L, and Gray N S. Targeting cancer with small molecule kinase inhibitors. Nature Reviews Cancer. 2009; 9:28-39.

P W Manley, Cowan-Jacob S W, Mestan J. Advances in the structural biology, design and clinical development of Bcr-Abl kinase inhibitors for the treatment of chronic myeloid leukaemia. Biochim. Biophis. Acta. 2005; 1754: 3-13.

P T Wan, et al. Mechanism of activation of the RAF-ERK signaling pathway by oncogenic mutations of B-RAF. Cell. 2004; 116:855-867.

Biological Procedure References

M A Fabian et al. A small molecule-kinases interaction map for clinical kinase inhibitors. Nat Biotechnol. 2005; 23:329-336.

M W Karaman et al. A quantitative analysis of kinase inhibitor selectivity. Nat Biotechnol. 2008; 26:127-132.

T A Carter et al Inhibition of drug-resistant mutants of ABL, KIT, and EGF receptor kinases. Proc. Natl. Acad. Sci. USA. 2005; 102:11011-11016.

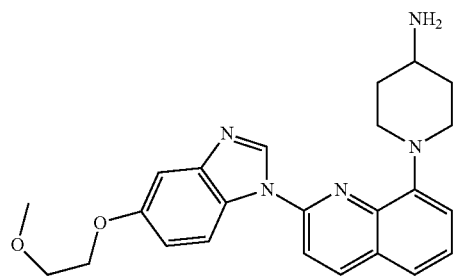 [SMILES: COCCOc1ccc2c(c1)ncn2-c1ccc2cccc(N3CCC(N)CC3)c2n1]

or a pharmaceutically acceptable salt or solvate thereof, wherein the cancer is selected from at least one of a leukemia, myeloma, myeloproliferative disease, or myelodysplastic syndrome, wherein the cancer has one or more FLT3 mutations selected from the group consisting of K663Q, N841I and R834Q.

2. The method of claim 1, wherein the compound is administered at least one of continuously, intermittently, systemically, or locally.

3. The method of claim 1, wherein the compound is administered orally, intravenously, or intraperitoneally.

4. The method of claim 1, wherein the compound is at least one of a Besylate, Phosphate, Lactate, Hydrochloride, Citrate, Acetate, Toluenesulphonate (tosylate) or Succinate salt.

5. The method of claim 1, wherein the therapeutically effective amount of compound is administered for as long as the subject is in need of treatment for the cancer.

6. The method of claim 1, wherein the compound is administered at least one of sequentially or concomitantly, with another pharmaceutical agent to the subject, and wherein the subject has been diagnosed with the cancer for the first time.

7. The method of claim 1, wherein the compound is administered as a single agent or in combination with another pharmaceutical agent to the subject, and wherein the subject has been diagnosed with the cancer for the first time.

8. The method of claim 1, wherein the compound is administered as a single agent or in combination with another pharmaceutical agent to the subject, and wherein the subject is a pediatric subject that has been diagnosed with the cancer for the first time.

What is claimed is:

1. A method of treating cancer in a subject, comprising: administering to the subject in need thereof a therapeutically effective amount of the compound of Formula I, i.e., CP-673,451:

9. The method of claim 1, further comprising the step of determining if the subject is relapsed/refractory to a prior FLT3 tyrosine kinase inhibitor.

10. The method of claim 1, further comprising the step of determining if the subject is relapsed/refractory to at least one of Sunitinib, Lestaurtinib/CEP-701, Quizartinib/AC220, Tandutinib/MLN-518, Midostaurin/PKC-412, AST-487, or Sorafenib, and then providing the CP-673,451 or a salt thereof.

11. The method of claim 1, wherein the compound is administered at least one of sequentially or concomitantly, with another pharmaceutical agent to the subject, and wherein the compound is administered to maintain remission of the cancer in the subject.

12. The method of claim 1, wherein the compound is administered at least one of sequentially or concomitantly, with another pharmaceutical agent to the subject, and wherein the subject is relapsed or refractory for the cancer.

13. The method of claim 1, wherein the compound is administered as a single agent or in combination with another pharmaceutical agent to the subject, and wherein the compound is administered to maintain remission of the cancer in the subject.

14. The method of claim 1, wherein the compound is administered as a single agent or in combination with another pharmaceutical agent to the subject, and wherein the subject is relapsed or refractory for the cancer.

15. The method of claim 1, wherein the compound is administered as a single agent or in combination with another pharmaceutical agent to the subject, and wherein the subject is a pediatric subject, and wherein the compound is administered to maintain remission of the cancer in the subject.

16. The method of claim 1, wherein the compound is administered as a single agent or in combination with another pharmaceutical agent to the subject, and wherein the subject is a pediatric subject that is relapsed or refractory for the cancer.

17. A method of treating cancer in a subject, consisting of:
administering to the subject in need thereof a therapeutically effective amount of the compound of Formula I, i.e., CP-673,451:

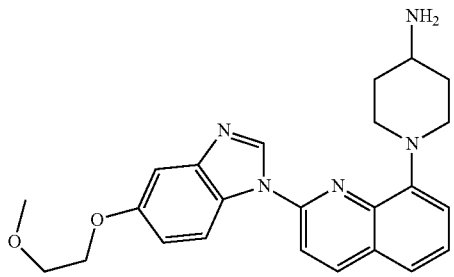 [SMILES: COCCOc1ccc2c(c1)ncn2-c1ccc2cccc(N3CCC(N)CC3)c2n1]

or a pharmaceutically acceptable salt or solvate thereof
wherein the cancer is a leukemia, myeloma, myeloproliferative disease, or myelodysplastic syndrome,
wherein the cancer has one or more FLT3 mutations selected from the group consisting of K663Q, N841I, and R834Q.

* * * * *

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide

<400> SEQUENCE: 1

Glu Ala Ile Tyr Ala Ala Pro Phe Ala Lys Lys Lys
1               5                   10
```